United States Patent
Meliani et al.

(10) Patent No.: US 11,460,496 B2
(45) Date of Patent: Oct. 4, 2022

(54) INHOMOGENEOUS TRANSMISSION LINE FOR DETERMINING THE PERMITTIVITY OF A DEVICE UNDER TEST IN A POSITION-RESOLVED MANNER

(71) Applicant: IHP GMBH—INNOVATIONS FOR HIGH PERFORMANCE MICROELECTRONICS/LEIBNIZ-INSTITUT FUR INNOVATIVE MIKROELEKTRONICS/LEIBNIZ—INSTIT FUR INNOVATIVE MIKROELECTRONIK, Frankfurt (DE)

(72) Inventors: Chafik Meliani, Berlin (DE); Subhajit Guha, Frankfurt (DE); Farabi Ibne Jamal, Frankfurt (DE)

(73) Assignee: IHP GMBH—INNOVATIONS FOR HIGH PERFORMANCE MICROELECTRONICS/LEIBNIZ-INSTITUT FUR INNOVATIVE MIKROELEKTRONIK, Frankfurt (DE)

( * ) Notice: Subject to any disclaimer, the term of this patent is extended or adjusted under 35 U.S.C. 154(b) by 202 days.

(21) Appl. No.: 15/547,353

(22) PCT Filed: Jan. 29, 2016

(86) PCT No.: PCT/EP2016/051887
§ 371 (c)(1),
(2) Date: Jul. 28, 2017

(87) PCT Pub. No.: WO2016/124489
PCT Pub. Date: Aug. 11, 2016

(65) Prior Publication Data
US 2018/0024176 A1  Jan. 25, 2018

(30) Foreign Application Priority Data
Feb. 2, 2015 (DE) .................. 10 2015 201 773.7

(51) Int. Cl.
*G01R 27/32* (2006.01)
*G01N 15/10* (2006.01)
(Continued)

(52) U.S. Cl.
CPC ......... *G01R 27/32* (2013.01); *G01N 15/1031* (2013.01); *G01N 22/00* (2013.01); *G01N 33/48728* (2013.01)

(58) Field of Classification Search
CPC ............ G01R 27/2664; G01R 27/2635; G01R 27/32; G01R 27/2617; G01R 27/2623;
(Continued)

(56) References Cited

U.S. PATENT DOCUMENTS 6,472,885 B1 * 10/2002 Green .................... G01N 22/00
324/638
7,705,607 B2 * 4/2010 Mashikian ........... G01R 31/083
324/533
(Continued)

FOREIGN PATENT DOCUMENTS

DE          10128213 A1   12/2002
DE     10 2006 052637 A1    5/2008
(Continued)

OTHER PUBLICATIONS

Andreas Penirschke, et al; "Non-Intrusive Microwave Mass Flow Meter Based on Two-dimensional Lefthanded Transmission Lines"; vol. 79, No. 3, Mar. 1, 2012; pp. 143-151.
(Continued)

*Primary Examiner* — Vinh P Nguyen
(74) *Attorney, Agent, or Firm* — Ware, Fressola, Maguire & Barber LLP

(57) ABSTRACT

A measuring carrier for position-resolved meteorological determination of a measurement variable dependent on the dielectric permittivity of a device under test. The measuring carrier has a supporting means comprising a measuring surface, to which the device under test can be applied, and a measuring transmission line which entirely or partially forms the measuring surface and comprises a multiplicity of transmission line cells for the purpose of transmitting a
(Continued)

radio-frequency measurement signal which can be injected at the input port. The measuring surface is structured in a cellular manner, wherein each of the transmission line cells has a cell-individual propagation constant with respect to the radio-frequency measurement signal in a state free of a device under test. This constant differs from the respective cell-individual constants of the other transmission line cells.

15 Claims, 7 Drawing Sheets

(51) Int. Cl.
    *G01N 22/00*     (2006.01)
    *G01N 33/487*     (2006.01)

(58) Field of Classification Search
    CPC .... G01R 33/16; G01N 15/1031; G01N 22/00; G01N 33/48728; G01N 27/221
    See application file for complete search history.

(56) References Cited

U.S. PATENT DOCUMENTS

| | | | |
|---|---|---|---|
| 7,973,539 B1* | 7/2011 | Kim | G01R 27/2641 |
| | | | 324/601 |
| 8,962,305 B2* | 2/2015 | Wu | G01N 27/221 |
| | | | 422/68.1 |
| 2006/0247896 A1 | 11/2006 | Goldfine et al. | |
| 2009/0160578 A1* | 6/2009 | Achour | H01P 1/203 |
| | | | 333/175 |
| 2009/0256817 A1 | 10/2009 | Perlin et al. | |
| 2011/0169511 A1* | 7/2011 | Nordin | G01N 33/48728 |
| | | | 324/692 |
| 2015/0381160 A1* | 12/2015 | Draxelmayr | H03K 17/161 |
| | | | 327/382 |
| 2016/0223669 A1* | 8/2016 | Assefzadeh | E21B 47/0002 |

FOREIGN PATENT DOCUMENTS

| | | |
|---|---|---|
| DE | 102007045234 A1 | 4/2009 |
| EP | 2574908 A1 | 4/2013 |
| WO | 2012/152618 A1 | 11/2012 |

OTHER PUBLICATIONS

Andreas Penirschke, et al; "Left-Handed Transmission Line Mass Flow Meter for Particulate Solids in Pipelines"; Sensor + Test Conference 2009; pp. 109-114.

* cited by examiner

INHOMOGENEOUS TRANSMISSION LINE FOR DETERMINING THE PERMITTIVITY OF A DEVICE UNDER TEST IN A POSITION-RESOLVED MANNER

CROSS REFERENCE TO RELATED APPLICATIONS

This application is the U.S. National Stage of International Application Number PCT/EP2016/051887 filed on Jan. 29, 2016, which application claims priority under 35 USC § 119 to German Patent Application No. 10 2015 201 773.7.4 filed on Feb. 2, 2015. Both applications are hereby incorporated by reference in their entirety.

TECHNICAL FIELD

The invention relates to a measuring carrier for spatially resolved meteorological determination of a measurement variable which is dependent on the dielectric permittivity of a device under test, or test object, to be applied to or placed on the measuring carrier.

It also relates to a measuring apparatus for spatially resolved determination of the a dielectric permittivity of a device under test and to a method for spatially resolved determination of the permittivity of a device under test.

BACKGROUND OF THE INVENTION

When characterizing materials, being able to perform spatially resolved measurements is often a necessity. With the aid of position-resolved measurements only, it is possible to detect inhomogeneties or random phenomena, for example in biomaterials.

One problem encountered thereby is that in many cases it is impossible, or not possible in a reliable manner, to position a sensor in the immediate vicinity of the device under test which is to be characterized, or in the immediate vicinity of a portion of the device under test. This limits the flexibility and accuracy of such measurements, so it is almost impossible in those cases to perform spatially resolved measurement of small structures such as biological cells, to observe cell growth, or to diagnose malignant cells.

For biological test objects, there are alternative solutions based on trap or marking techniques (electrical or mechanical), but such measurement techniques can affect the sample characteristics being measured, thus distorting the measurements obtained, or increasing the effort involved in processing them.

Other known solutions for position-resolved measurement are based on using many individual sensors, as described in US 2006/0247896, for example. However, using many sensors means that many inputs and outputs have to be realized in the measuring device. This greatly limits the opportunities for miniaturization and hence also the maximum resolution that can be achieved, as well as the options for realization.

SUMMARY OF THE INVENTION

Embodiments of the present invention shall now be described.

According to a first aspect of the invention, a measuring carrier is provided for spatially resolved metrological determination of a measurement variable dependent on the dielectric permittivity of a device under test or test object to be applied to or placed on the measuring carrier, said measuring carrier comprising a supporting means (support) with a measuring surface, to which the device under test can be applied, a measuring transmission line of the measuring carrier, which entirely or partially forms the measuring surface and is designed as an electrical series circuit comprising a multiplicity of transmission line cells for the purpose of transmitting an electromagnetic radio-frequency measurement signal which can be injected, the measuring surface therefore being structured in a cellular manner, wherein each of the transmission line cells of the measuring transmission line per se has a cell-individual propagation constant with respect to the radio-frequency measurement signal in a state free of a device under test, which propagation constant differs from the respective cell-individual propagation constants of the other transmission line cells, and is designed to assume a cell-individual propagation constant which differs from the state free of a device under test in a measuring state when the device under test is applied to the transmission line cell, in such a way that a change in the respective cell-individual propagation constant of each of the transmission line cells in the measuring state in comparison to the state free of the device to be tested causes a respective identifiable change component of a total change in a measurement variable which can be detected on the basis of the radio-frequency measurement signal and which is dependent on the dielectric permittivity of the measuring transmission signal as a whole.

The present invention provides a measuring carrier with which it is easy to carry out position-resolved measurements of the permittivity of the device under test. The invention is based on the concept of an inhomogeneous transmission line having portions that have different propagation constants for electromagnetic waves. Propagation of an electromagnetic signal via such an inhomogeneous transmission line is affected by the propagation constants of the transmission line portions and of the surrounding material. If the permittivity of the material in the surroundings changes, the propagation of the signal will be affected accordingly. Based on the change in the propagation constant, it is thus possible to determine the position of the material and to analyze the material. The position of the material is derived from the different propagation constants of the individual transmission line portions.

With the measuring carrier described here, it is possible with just one single measurement, using a single signal source whose radio-frequency signal is conducted through the measuring transmission line and therefore through every single one of the transmission line cells, due to their connection in series, to detect a measurement variable which allows the permittivity of the device under test to be determined in all the transmission line cells. Since the transmission line cells provide the measuring surface with a cellular structure, it is possible on the basis of a single measurement to identify a spatially resolved measurement data field, on the basis of which the permittivity of the device under test can be determined in the individual transmission line cells.

The measuring carrier is a component which in some embodiments can also be traded independently of an associated measuring apparatus, and the structure of which is what makes the measurement technique described in the foregoing possible in the first place.

Embodiments of the measuring carrier according to the invention shall now be described. The additional features of the embodiments may be combined with each other to form other embodiments, unless they are explicitly described as alternatives to each other. In one embodiment of the measuring carrier, the transmission line cells each form an LC gate. The cell-individual propagation constant is realized by a cell-individually predetermined capacitance of the respective LC gate. An LC gate is understood here to be a circuit arrangement consisting of at least one inductive and at least one capacitive element. In this embodiment, each transmission line cell affects, with its individual capacitance, a surface element of the measuring surface which it forms. In one variant of this embodiment, the inductances of the LC gates are the same in all the transmission line cells. Transmission line cells with ohmic resistance or derivative components, which are negligible for the purposes of the measurement involved here when suitable frequencies are used for the radio-frequency measurement signal, are also referred to as LC gates.

Depending on frequency range and application, the measuring carrier can be realized in the form of a circuit board having printed transmission line structures (printed circuit board, PCB) or produced monolithically using the methods of semiconductor technology.

Various other variants of this embodiment are possible. In one variant of the measuring carrier according to this embodiment, a first transmission line cell has a first predetermined capacitance. The other predetermined capacitances of the other transmission line cells are each predetermined as the product of a cell-Individual power of a specified factor and the first predetermined capacitance. Measurement resolution and measurement dynamics can be specifically tailored using said factor. The larger the factor, the greater the dynamic range. The dynamic range corresponds to a measurement range which is determined by the propagation constant and in which the permittivity s can be separately determined for the respective line transmission cells. In another variant, a dynamic range varies individually for each cell. However, this dynamic range can be relatively equal for all capacitances, that is to say in relation to the respective capacitance. This can be explained with reference to an example. For all transmission line cells, the dynamic range may comprise, for example, the value of the capacitance of the respective transmission line cells. For a particular change in permittivity there is a dynamic range (of the change in capacitance) from $$\frac{C}{2} \text{ to } \frac{3}{2}C,$$

where C is the respective capacitance of the respective transmission line cell. For a first transmission line cell having a capacitance of $C=C_0$, the resultant dynamic range is from $$\frac{C_0}{2} \text{ to } \frac{3C_0}{2}.$$

For a second transmission line having a capacitance of $C=A \cdot C_0$, the dynamic range is from $$\frac{A \cdot C_0}{2} \text{ to } \frac{3A \cdot C_0}{2},$$

and for a third transmission line having a capacitance of $C=A^2 \cdot C_0$, the range is from $$\frac{A^2 \cdot C_0}{2} \text{ to } \frac{3A^2 \cdot C_0}{2}.$$

A sample of material placed on a transmission line cell of the transmission line causes a phase difference in the transmitted signal in the dynamic range of the respective transmission line cell. For the example above, the following phase differences will therefore result. If there is a test object lying on the first transmission line portion ($C=C_0$), then this will cause a phase difference ranging from $$\frac{1}{\sqrt{\frac{C_0}{2} \cdot L_0}} \text{ to } \frac{1}{\sqrt{\frac{3C_0}{2} \cdot L_0}},$$

where $L_0$ is the inductance of the transmission line portion. In the present example, the inductance is assumed to be equal for all the transmission line portions. If there is a test object lying on the second transmission line portion ($C=A \cdot C$), this will result in a phase difference ranging from $$\frac{1}{\sqrt{\frac{AC_0}{2} \cdot L_0}} \text{ to } \frac{1}{\sqrt{\frac{3AC_0}{2} \cdot L_0}}.$$

If the test object is lying on the third transmission line portion ($C=A^2 \cdot C_0$), then this will cause a phase difference ranging from $$\frac{1}{\sqrt{\frac{A^2 C_0}{2} \cdot L_0}} \text{ to } \frac{1}{\sqrt{\frac{3A^2 C_0}{2} \cdot L_0}}.$$

This means that it is possible to identify the transmission line portion on which the sample of material from the range in which the phase difference is determined. The measured phase differences can be assigned to the individual transmission line portions.

In a first group of embodiments, the measuring carrier has two terminals, one forming an input port for injecting the radio-frequency measurement signal, the other forming an output port for outputting the radio-frequency measurement signal transmitted through the measuring transmission line to the measuring apparatus, thus allowing the transmission to be measured. Alternatively or in addition thereto, another group of embodiments is configured for reflectometry in which an input port and an output port of the measuring carrier are formed by the same port.

In one embodiment of the measuring carrier, the inductances of all the transmission line portions are the same. This means that the transmission line portions differ solely by their different capacitances. In other embodiments in which the transmission line cells each form an LC gate, the cell-individual propagation constant is realized by a cell-individually a predetermined inductance of the respective LC gate. In some such embodiments, the capacitance of all the transmission line cells is identical. In this case also, the cell-individual configuration is realized in one example in such a way that a first transmission line cell has a first predetermined inductance and other predetermined inductances of the other transmission line cells are predetermined as a product of a cell-individual power of a specified factor and the first predetermined inductance. If the transmission line portions have different inductances, impedance matching of the line is improved and measurement is simplified. Furthermore, it is possible for measurement sections to be formed from a plurality of transmission line cells.

In another embodiment of the measuring carrier, at least one transmission line cell forms a left-handed portion of the transmission line. A left-handed transmission line, or a left-handed portion of the latter, has a negative permittivity and thus a negative propagation constant for the radio-frequency measurement signal. Left-handed structures have a similar or even a higher sensitivity than right-handed structures, given similar dimensions. For example, a transmission line may have a first transmission line cell which forms a normal, that is to say right-handed line portion, and a second transmission line cell having a left-handed structure.

Since the propagation constants for left-handed and right-handed structures typically have different frequency dependencies of permittivity, it is possible by detecting changes in the propagation constants in different frequency ranges of the radio-frequency measurement signal to determine not only different permittivities but also the locations of those different permittivities.

It is particularly advantageous when the measuring transmission line as a whole, as a series circuit comprising left-handed and right-handed portions in the form of the respective transmission line cells, has a propagation constant of zero for the radio-frequency measurement signal in a state free of a device under test. In this embodiment, a material placed on the transmission line portion causes a change in the propagation constant in either the positive or the negative direction.

In another embodiment of the measuring carrier, the measuring surface is additionally formed by a second measuring transmission line electrically connected in parallel to the measuring transmission line described in the foregoing. Each transmission line cell of the first measuring transmission line is coupled with an associated transmission line cell of the second measuring transmission line by means of a respective active electronic component, preferably by means of a transistor. In this embodiment, the measuring carrier thus has a second measuring transmission line in the supporting means, said measuring carrier being connected in parallel and actively coupled to the (first) measuring transmission line. In this embodiment of the invention, a partial amplitude of the radio-frequency measurement signal, which is transmitted via the first measuring transmission line, is injected cell by cell into the second transmission line. A device under test which is arranged on one of the portions of the first or the second transmission line alters the coupling coefficient for the respective transmission line cells and thus the propagation constants and the scatter matrix parameters, said scatter matrix parameters also being referred to as S-parameter matrices, as can be measured on the basis of the radio-frequency signal provided at the output port. It is therefore possible, with this embodiment also, to determine the location and the permittivity of a device under test.

According to the invention, the measuring transmission line forms at least one portion of the measuring surface, as already mentioned. This can be realized, for example, in the form of a direct contact between the measuring transmission line, meaning the respective transmission line cells, and a device under test to be placed thereon. In another embodiment of the measuring carrier, the transmission line has a protective layer with which the device under test placed thereon for measurement has direct contact. For the purposes of this embodiment such a protective layer is to be understood as part of the measuring transmission line. With this embodiment it is possible to protect the transmission line against harmful effects of the environment or the device under test, for example corrosion.

According to a second aspect, the invention relates to a measuring apparatus for spatially resolved determination of the dielectric permittivity of a device under test, comprising:
  a controller designed to supply a predetermined radio-frequency measurement signal;
  an output interface for supplying the radio-frequency measurement signal to a measuring carrier according to any one of claims 1 to 9 and an input interface for receiving from the measuring carrier the radio-frequency measurement signal transmitted through the measuring transmission line of the measuring carrier; and
  an evaluation unit which is designed to detect a measurement variable which is dependent on the propagation constant of the measuring transmission line, on the basis of the radio-frequency signal received in the measuring state from the input interface when the device under test is applied, to compare the detected measurement variable with a measurement variable sample determined in the measuring transmission line in the state free of the device under test and to determine change components of the propagation constant on the basis of the result of comparison and pre-stored cell-individual parameters, and to calculate cell-individual permittivity values of the device under test using said change components.

It should be understood that a measurement variable sample can take different forms. For example, the measurement variable sample may contain calibration values or signal patterns.

The measuring apparatus shares the advantages of the measuring carrier according to the first aspect of the invention. Some of its embodiments shall now be described.

In one preferred form of the invention, the controller is designed to control generation of the radio-frequency signal as a sequence of signals having different frequencies.

The pre-stored cell-individual parameters are suitable for computing a cell-individual propagation constant of the respective transmission line cell in the state free of a device under test. They are stored either either in the measuring apparatus, for example in the evaluation unit itself, or may be detected as part of an additional measurement.

In one variant, the measuring apparatus is monolithically integrated with the measuring carrier.

According to a third aspect the invention relates to a method for spatially resolved determination of the permittivity of a device under test, comprising the steps of
  providing a measuring carrier according to the first aspect of the invention or one of its disclosed embodiments;
  applying the device under test to the supporting means of the measuring carrier;
  supplying a radio-frequency measurement signal to the measuring transmission line of the measuring carrier;
  detecting the radio-frequency measurement signal which is transmitted through a the measuring transmission line, for example at an output port (transmission) or at an input port (reflection) of the measuring carrier used for supplying the radio-frequency measurement signal;

determining a measurement variable dependent on the propagation constants of the measuring transmission line on the basis of the detected radio-frequency measurement signal;

comparing the determined measurement variable with a measurement variable sample determined in the measuring transmission line in the state free of a device under test determining change components of the propagation constants cell-individually on the basis of the result of comparison and on the basis of pre-stored cell-individual parameters;

determining cell-individual permittivity values of the device under test on the basis of the calculated cell-individual change components.

In a preferred embodiment of the invention, the method is performed several times at different frequencies of the radio-frequency measurement signal.

Suitable measurement methods in the context of the invention are S-parameter measurements, for example, or transmission measurements or reflection measurements, or even measurements of line gain and loss. The losses measured can be used to calculate the permittivity values of those parts of the device under test arranged on the individual transmission line portions.

The measuring apparatus and the method for measuring permittivity share the advantages of the measuring carrier according to the first aspect of the invention and have matching embodiments. Embodiments of the invention are also described in the claims.

BRIEF DESCRIPTION OF THE DRAWINGS

Other embodiments of the measuring carrier according to the invention and of measuring apparatus and the method for measuring permittivity shall now be described with reference to the Figures, in which.

DETAILED DESCRIPTION

Figure 1:
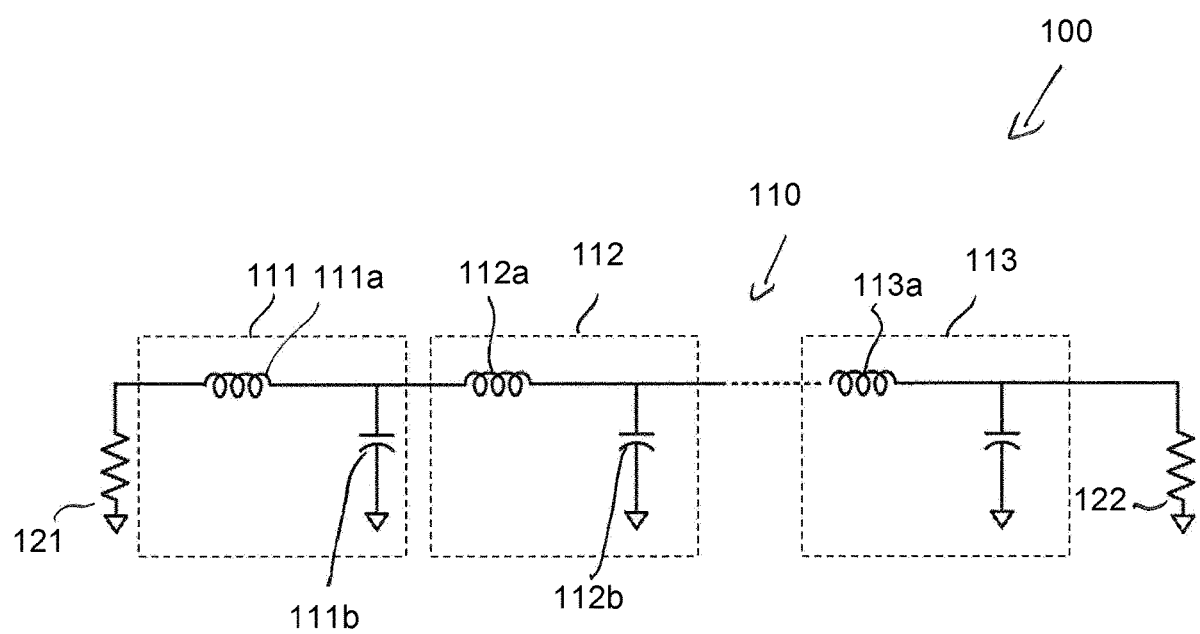
FIG. 1 shows a schematic circuit diagram of an embodiment of a measuring carrier according to the first aspect of the invention.

FIG. 1 shows a schematic circuit diagram of an embodiment of a measuring carrier 100 according to the first aspect of the invention.

Measuring carrier 100 has a measuring transmission line 110, which is used for transmitting a radio-frequency measurement signal and which has a plurality of transmission line cells electrically connected in series, represented here in the form of a simplified example comprising three transmission line cells 111, 112, 113. As a whole, the transmission line cells form a measuring surface which is appropriately designed for the respective application and which accordingly has a cellular structure. Each of transmission line cells 111, 112, 113 has a cell-individual propagation constant for the radio-frequency measurement signal, which differs from the propagation constants of the other transmission line cells. Transmission line cells 111, 112, 113 each have an inductance 111a, 112a, 113a forming part of the line, and a capacitance 111b, 112b, 113b. Different transmission line cells 111, 112, 113 have different capacitances in the present embodiment. There is also variation, therefore, in the respective propagation constants of the different transmission line cells, which contribute to the propagation constant of the measuring transmission line as a whole.

If a device under test is placed on the measuring surface of the measuring carrier, it comes into contact with the transmission line cells and exerts an influence, with its dielectric permittivity at the respective location, on the cell-individual propagation constants of the different transmission line cells occupied by the device under test and thus results in cell-individual contributions to losses and phase differences of the transmitted signal. The oscillation characteristics are therefore altered.

In the present embodiment, each transmission line cell 111, 112, 113 has a dynamic range which varies by the capacitance of the respective transmission line portion and in which the permittivity a can be determined.

The capacitances of the transmission line cells are selected in the present example such that a first transmission line portion 111 has a first capacitance, and the other capacitances of the other transmission line cells 112, 113 are equal to the product of a factor A, or the increasing powers thereof, and the first capacitance. Depending substantially on the capacitance and the inductance of the respective transmission line cell, the latter contributes only a cell-individual share to the losses and phase differences of the radio-frequency measurement signal when transmitting through the measuring transmission line. Those shares are designed so that the contributions of the participant transmission line cells can be clearly inferred from the total measured phase difference or total loss. In this way, it is possible to draw conclusions from the measured change regarding the permittivity of the device under test causing said change at the location of the respective transmission line cell.

In another embodiment of the invention, which is not shown here, transmission line cells 111, 112, 113 also have different inductances, in addition to different capacitances.

In the present embodiment, the measuring transmission line has two terminals 121, 122 for a measuring apparatus, which form an input port and an output port of the measuring carrier. This means there are two ways of performing measurements, the first being transmission measurement, in which both terminals 121, 122 are used and the transmission of a signal via transmission line 110 is measured. However, measuring carrier 100 also allows measurement at only one of terminals 121, which thus forms both the input port and the output port. To that end, the second terminal 122 is terminated with a short circuit or an open circuit, so that there is a full reflection at terminal 122. The measuring distance doubles as a result. Measurement is performed analogously to measurement of transmission, the only difference being that the measured phase response and the losses on the line are for the double distance. When measurement is performed at only one terminal, specific terminal impedances can be additionally integrated in the setup, instead of the short circuit or the open circuit. With the aid of these additional impedances, it is possible to influence the measurement conditions and to achieve greater measurement accuracy.

Figure 2:
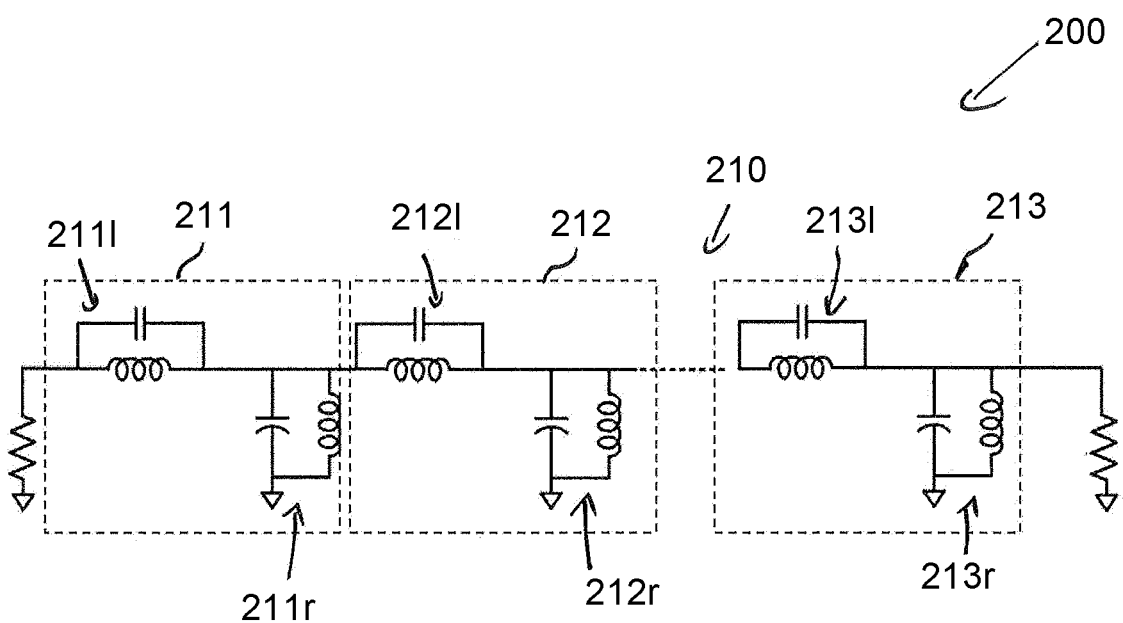
FIG. 2 shows a schematic circuit diagram of another embodiment of a measuring carrier according to the first aspect of the invention.

FIG. 2 shows a circuit diagram of another embodiment of a measuring carrier 200 according to the first aspect of the invention. In contrast to the measuring carrier shown in FIG. 1, transmission line cells 211, 212, 213 of measuring transmission line 210 in the embodiment shown are left-handed structures 211l, 212l, 213l, in combination with right-handed structures 211r, 212r, 213r. The left-handed and right-handed parts of the respective transmission line portions are designed in such a way that the propagation constant as a whole is equal to zero. This results from the negative cell-individual propagation constants of the left-handed portions in the respective transmission line cells and the positive cell-individual propagation constants of the right-handed portions in the other respective transmission line cells. Thus, devices under test which are arranged on a respective one of the transmission line cells alter the respective cell-individual propagation constant in the positive or negative direction. This means that it is possible to determine, cell-individually and thus with spatial resolution, a spatially dependent dielectric permittivity of the material of the device under test at the differently occupied transmission line cells 211, 212, 213. Measurement at a measuring carrier 200 as shown in FIG. 2 is performed analogously to the variants described with reference to FIG. 1.

Figure 3:
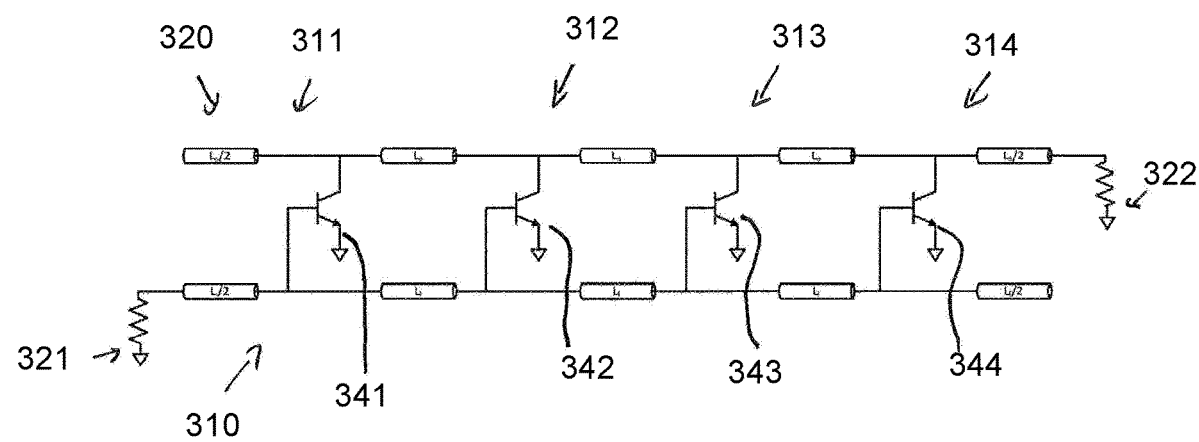
FIG. 3 shows a schematic circuit diagram of a third embodiment of a measuring carrier according to the first aspect of the invention.

FIG. 3 shows a schematic circuit diagram of a third embodiment of a measuring carrier 300 according to the first aspect of the invention. Measuring carrier 300 has two measuring transmission lines 310, 320, which are electrically connected in parallel to each other and which are actively coupled to each other. Coupling is via active components, and via BJT bipolar transistors in the embodiment shown. The electromagnetic wave of the radio-frequency measurement signal which propagates through the measuring transmission lines from terminal 321 serving as an input port is coupled in one direction to a signal of the second transmission line via bipolar transistors 341, 342, 343, 344. A device under test arranged on one of the transmission line cells 311, 312, 313, 314 alters the coupling coefficient for that transmission line cell and thus the propagation constant or scatter matrix parameter.

Figure 4:
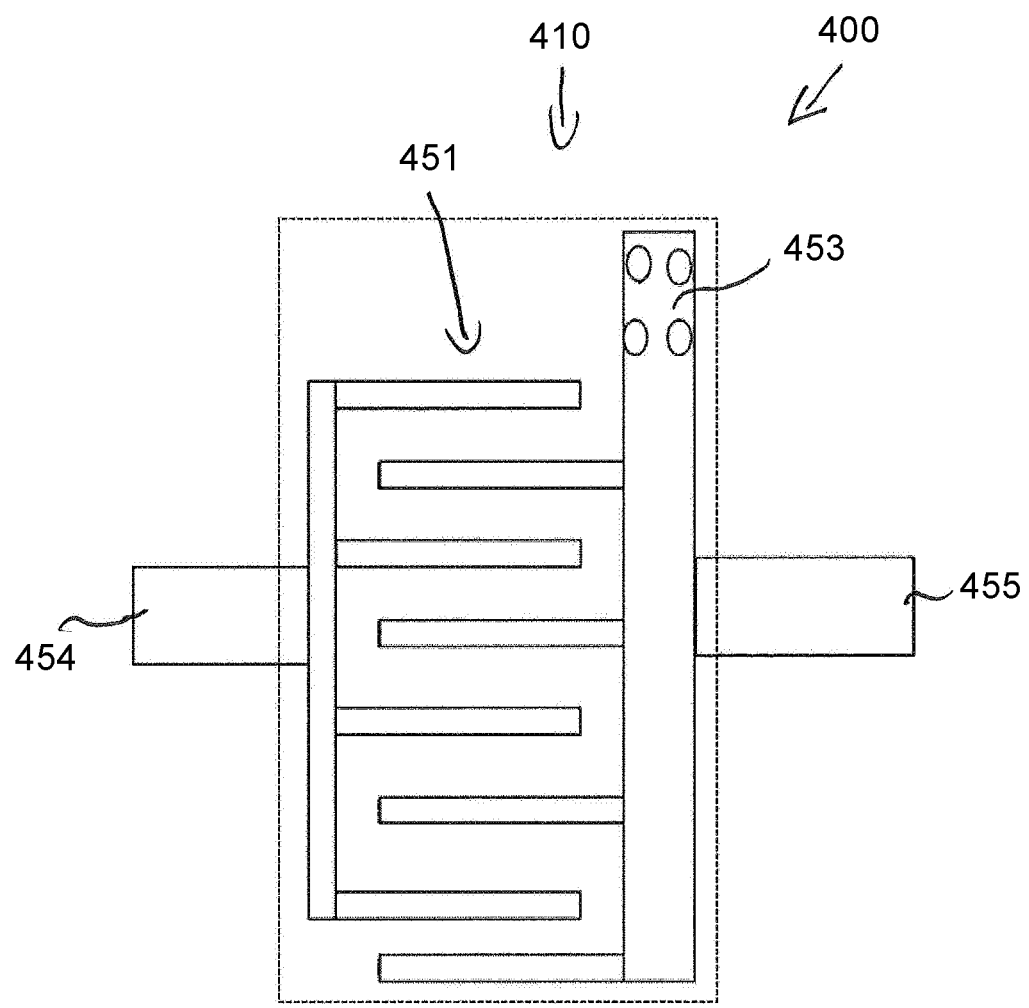
FIG. 4 shows a schematic view of a fourth embodiment of a measuring carrier according to the first aspect of the invention.

FIG. 4 shows a detail of a fourth embodiment of a measuring carrier according to the first aspect of the invention. The embodiment of measuring carrier 400 shown here can be realized in both a hybrid form, for example on a printed circuit board, and also monolithically, for example on a chip. Hybrid realization makes sense for measuring carriers for test frequencies ranging from 1 GHz to 5 GHz, whereas monolithic realization is recommended for higher frequencies. Frequencies significantly lower than 1 GHz are not envisaged here. The detail of a transmission line 410 of the measuring carrier shown here has a transmission line cell which is formed by left-handed portions. The intermeshing finger-like structures 451 shown here form a capacitance. Terminals 454 and 455 constitute electrodes. The capacitance is connected by one or several vias 453.

Figure 5:
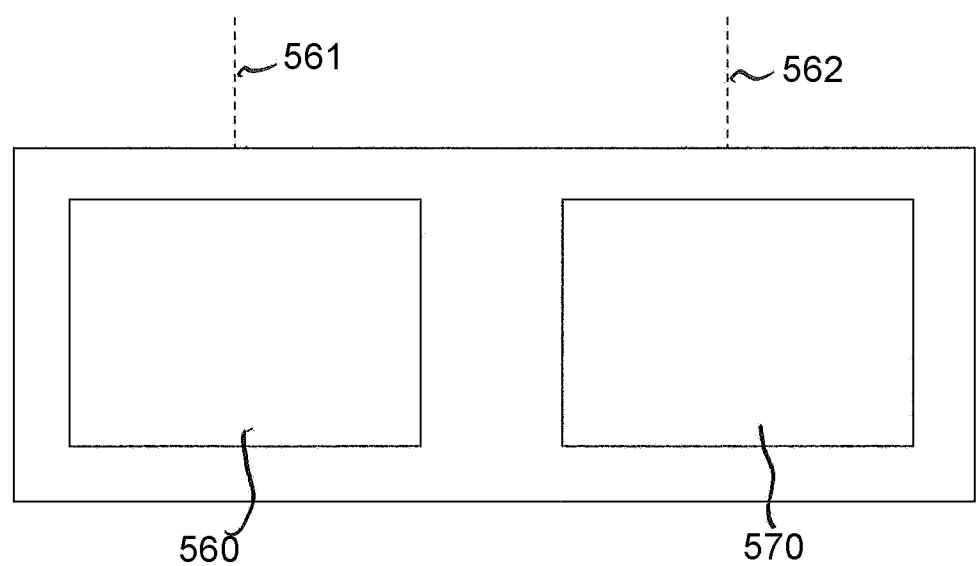
FIG. 5 shows a schematic view of an embodiment of a measuring apparatus according to the second aspect of the invention.

FIG. 5 shows a schematic view of an embodiment of a measuring apparatus 500 according to the second aspect of the invention. Measuring apparatus 500 comprises a controller 560 and an evaluation unit 570.

Controller 560 is configured to trigger generation of a signal, i.e., to provide a predetermined radio-frequency measurement signal.

The measuring apparatus also has an output interface 561 for supplying the radio-frequency measurement signal at the input port of a measuring carrier, as shown for example in FIG. 1, and an input interface 562 for receiving the radio-frequency measurement signal transmitted through the measuring transmission line of the measuring carrier from the output port of the measuring carrier.

Evaluation unit 570 is designed to detect a measurement variable which is dependent on the propagation constant of the measuring transmission line, on the basis of the radio-so frequency signal received in the measuring state from the input interface when the device under test is applied, to compare the detected measurement variable with a measurement variable sample determined in the measuring transmission line in the state free of the device under test and to determine change components of the propagation constant on the basis of the result of comparison and pre-stored cell-individual parameters, and to calculate cell-individual permittivity values of the device under test using said change components. The cell-individual parameters are the capacitance, inductance or coupling coefficient of the transmission line portion formed by the respective transmission line cell. These parameters allow conclusions to be drawn about the propagation of the radio-frequency measurement signal in the respective transmission line cell and about the change in propagation when a device under test is arranged on a transmission line—and also conclusions, therefore, about the position and the permittivity of the device under test at the location of the occupied transmission line cells, namely about the change in propagation.

Figure 6:
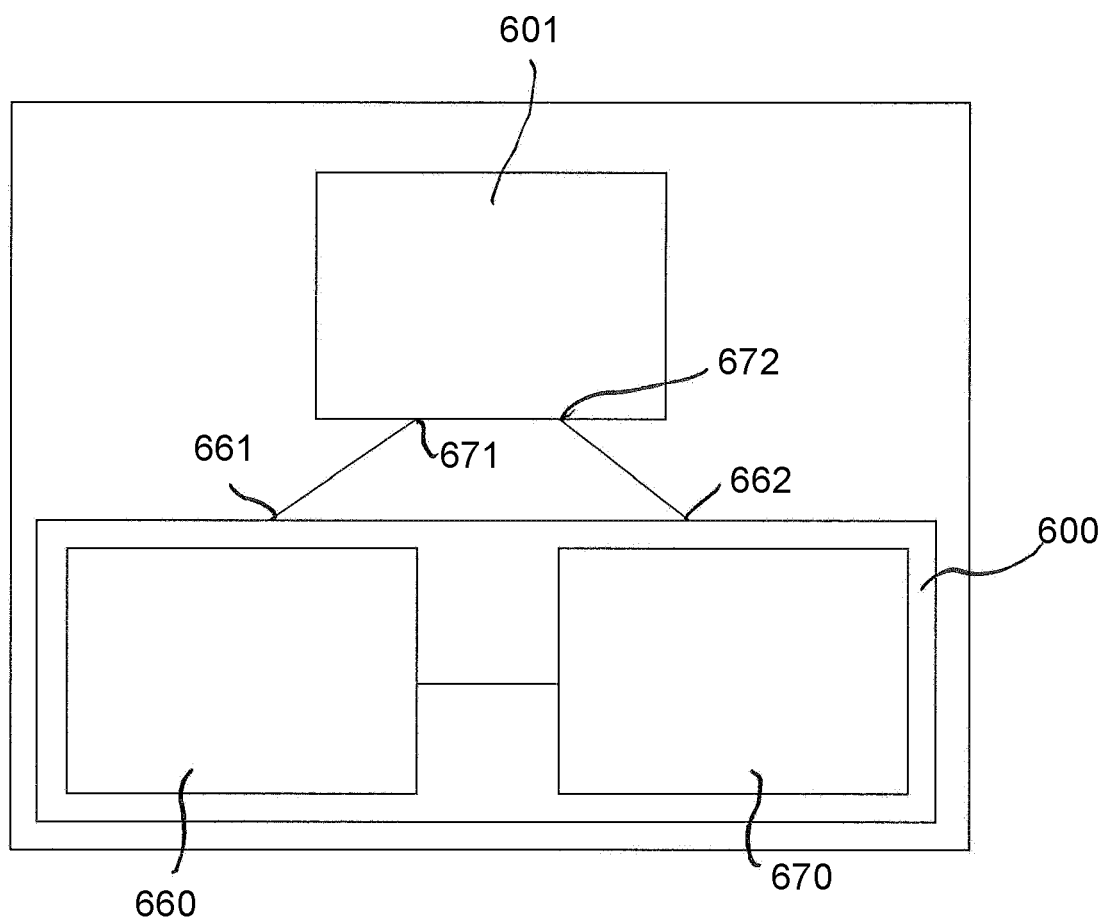
FIG. 6 shows a schematic view of an embodiment of an integrated measuring apparatus according to the third aspect of the invention.

FIG. 6 shows a schematic view of a measuring apparatus 600 which is monolithically integrated with measuring carrier 601. The Integrated measuring apparatus 600, like the measuring apparatus in FIG. 5 which has already been described, has a controller 660, an evaluation unit 670, an output interface 661 and an input interface 662. Output interface 661 is connected to an input port 671 of measuring carrier 601, and input interface 662 is connected to an output port 672 of measuring carrier 601. Monolithic integration of measuring apparatus 600 with measuring carrier 601 allows a measuring device for determining permittivity to be of compact design.

Figure 7:
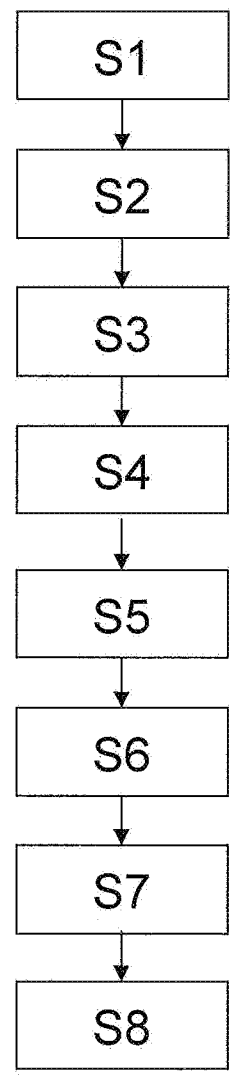
FIG. 7 shows a schematic view of an embodiment of a method according to the fourth aspect of the invention.

FIG. 7 shows in schematic form a method for position-solved measurement of the permittivity values of an object, according to the third aspect of the invention. In step S1, a measuring carrier according to a first aspect of the Invention is firstly provided, as shown by way of example in FIG. 1. In step S2, the device under test is then placed on the support surface of the measuring carrier. In step S3, an electromagnetic radio-frequency measurement signal is provided at the input port of the measuring transmission line of the measuring carrier. In step S4, the radio-frequency measurement signal transmitted through the measuring transmission line is then received at the output port of the measuring carrier, and a measurement variable which is dependent on the propagation constant of the measuring transmission line s determined on the basis of the detected so radio-frequency measurement signal (step S5). The determined measurement variable is then compared with a measurement variable sample determined in the measuring transmission line in the state free of a device under test (step S6). In step S7, the cell-Individual change components of the propagation constant are determined on the basis of the result of comparison and pre-stored cell-individual parameters, and in step S8 the cell-individual permittivity values of the device under test are determined on the basis of the calculated cell-individual change components.

The invention claimed is:

1. A measuring carrier for spatially resolved metrological determination of a measurement variable dependent on a dielectric permittivity of a device under test to be applied to the measuring carrier, comprising:
a measuring transmission line which entirely or partially forms a measuring surface, and wherein the measuring transmission line is designed as an electrical series circuit of a multiplicity of transmission line cells for the purpose of transmitting an electromagnetic radio-frequency measurement signal which injected, the measuring surface therefore being structured in a cellular manner, wherein
each of the transmission line cells of the measuring transmission line per se
has a cell-individual propagation constant with respect to the radio-frequency measurement signal in a state free of any device under test, which propagation constant differs from the respective cell-individual propagation constants of the other transmission line cells, and
is configured to have a cell-individual propagation constant in a measuring state, when the a device under test is applied to the transmission line cell, which differs from the cell-individual propagation constant of the state free of any device under test in such a way that
a change in the respective cell-individual propagation constant of each of the transmission line cells in the measuring state in comparison to the state free of the device to be tested causes a respective identifiable change component of a total change in the measurement variable which is detectable on the basis of the radio-frequency measurement signal and which is dependent on the dielectric permittivity of the measuring transmission signal as a whole.

2. The measuring carrier according to claim 1, in which the transmission line cells each form an LC gate, and wherein the cell-individual propagation constant is realized by a cell-individually predetermined capacitance of the respective LC gate.

3. The measuring carrier according to claim 2, in which a first transmission line cell has a first predetermined capacitance and other predetermined capacitances of the other transmission line cells are predetermined as a product of a cell-individual power of a specified factor and the first predetermined capacitance.

4. The measuring carrier according to claim 1, in which the transmission line cells each form an LC gate, and in which the cell-individual propagation constant is realized by a cell-individually predetermined inductance of the respective LC gate.

5. The measuring carrier according to claim 4, in which a first transmission line cell has a first predetermined inductance and other predetermined inductances of the other transmission line cells are predetermined as a product of a cell-individual power of a specified factor and the first predetermined inductance.

6. The measuring carrier according to claim 1, in which at least one transmission line cell forms a left-handed portion of the measuring transmission line.

7. The measuring carrier according to claim 6, in which the measuring transmission line as a whole, as a series circuit comprising left-handed and right-handed portions in the form of the respective transmission line cells, has a propagation constant of zero for the radio-frequency measurement signal in a state free of a device under test.

8. The measuring carrier according to claim 1, in which the measuring surface is additionally formed by a second measuring transmission line electrically connected in parallel to the measuring transmission line, and in which each transmission line cell of the first measuring transmission line is coupled with an associated transmission line cell of the second measuring transmission line by a respective active electronic component.

9. The measuring carrier according to claim 8, wherein the respective active electronic component is a transistor.

10. The measuring carrier according to claim 1, in which the measuring transmission line has a protective layer which is designed to protect the material of the measuring transmission line from a mechanical or chemical interaction with the device under test to be applied.

11. A measuring apparatus for position-resolved determination of a dielectric permittivity of a device under test, comprising:
a controller designed to supply a predetermined radio-frequency measurement signal;
an output interface for supplying the radio-frequency measurement signal to a measuring carrier according to claim 1 and an input interface for receiving from the measuring carrier the radio-frequency measurement signal transmitted through the measuring transmission line of the measuring carrier; and
an evaluation unit which is configured to detect a measurement variable which is dependent on the propagation constant of the measuring transmission line, on the basis of the radio-frequency signal received in the measuring state from the input interface when the device under test is applied, to compare the detected measurement variable with a measurement variable sample determined in the measuring transmission line in the state free of the device under test and to determine change components of the propagation constant on the basis of the result of comparison and pre-stored cell-individual parameters, and to calculate cell-individual permittivity values of the device under test using said change components.

12. The measuring apparatus according to claim 11, in which the pre-stored cell-individual parameters are suitable for computing a cell-individual propagation constant of the respective transmission line cell in the state free of a device under test.

13. The measuring apparatus according to claim 11, in which the controller is configured to supply the radio-frequency measurement signal as a sequence of several signals having several different frequencies.

14. The measuring apparatus according to claim 11, which is monolithically integrated with the measuring carrier.

15. A method for position-resolved determination of the permittivity of a device under test, comprising:
providing a measuring carrier according to claim 1;
applying the device under test to the measuring surface of the measuring carrier;
supplying an electromagnetic radio-frequency measurement signal to the measuring transmission line of the measuring carrier;
detecting the radio-frequency measurement signal which is transmitted through the measuring transmission line;
determining a measurement variable dependent on the propagation constants of the measuring transmission line on the basis of the detected radio-frequency measurement signal;

comparing the determined measurement variable with a measurement variable sample determined in the measuring transmission line in the state free of a device under test;

determining change components of the propagation constants cell-individually on the basis of the result of comparison and on the basis of pre-stored cell-individual parameters; and determining cell-individual permittivity values of the device under test on the basis of the calculated cell-individual change components.

* * * * *